United States Patent [19]

Joyce

[11] 4,100,789
[45] Jul. 18, 1978

[54] FLUIDIC PARTIAL PRESSURE SENSOR

[75] Inventor: James W. Joyce, Rockville, Md.

[73] Assignee: The United States of America as represented by the Secretary of the Army, Washington, D.C.

[21] Appl. No.: 819,745

[22] Filed: Jul. 28, 1977

[51] Int. Cl.² .................................................. G01N 31/00
[52] U.S. Cl. ......................................................... 73/23
[58] Field of Search ................. 73/23, 196; 128/140 R, 128/142 G; 137/88

[56] References Cited

U.S. PATENT DOCUMENTS

| 3,756,068 | 9/1973 | Villarroel et al. | 73/23 |
| 3,771,348 | 11/1973 | Villarroel | 73/23 |
| 4,008,601 | 2/1977 | Woods | 73/23 |
| 4,057,205 | 11/1977 | Vensel | 137/88 X |

OTHER PUBLICATIONS

Harry Diamond Laboratories Report HDL-TM-73-9, "Analog Flueric Gas Concentration Sensor" by Villarroel et al. (6-73).
Harry Diamond Laboratories Report HDL-TM-75-17, "Fluidic Sensors for Life Support Systems", by Joyce et al. (10-75).

Primary Examiner—James J. Gill
Attorney, Agent, or Firm—Nathan Edelberg; Robert P. Gibson; Saul Elbaum

[57] ABSTRACT

A fluidic partial pressure sensor for obtaining a direct indication of the partial pressure of a gas constituent in a mixture relative to a reference gas. A fluidic bridge's geometry is so designed and structured that if the pressure across the bridge is maintained constant, the pressure differential between the two channels thereby becomes directly proportional to the partial pressure of the gas constituent of interest. A typical bridge sensor therefore can provide a direct indication of partial pressure. The geometry of the bridge network is chosen so that the sensor gain constant varies linearly with ambient pressure.

8 Claims, 6 Drawing Figures

FLUIDIC PARTIAL PRESSURE SENSOR

RIGHTS OF THE GOVERNMENT

The invention described herein may be manufactured, used and licensed by or for the United States Government for governmental purposes without the payment to me of any royalty thereon.

BACKGROUND OF THE INVENTION

1. Field of the Invention

This invention is in the field of fluidic devices and, more specifically, is related to fluidic partial pressure sensors which obtain direct indications of a gas constituent in a mixture.

2. Description of the Prior Art

A low cost partial pressure sensor would certainly be an asset in systems that require a constant partial pressure of a gas in a mixture no matter at what ambient pressures the system rests. An example of such system would be an oxygen control system needed for the control of life-support systems aboard aircraft where it is desirable to provide the ground equivalent of oxygen to the aircraft operators regardless of altitude.

Most prior art systems required the measurement of two parameters, gas concentration and ambient pressure, the product of which is, by definition, partial pressure. Therefore, in addition to the measurements, there must be a computation to determine how much oxygen is to be admixed with the ambient air. Because such systems generally required the use of two devices for measurement and computational equipment in order to schedule the correct amount of oxygen to the aircraft, these systems were not responsive to situations involving varying ambient pressures and certainly not simple.

U.S. Pat. No. 4,008,601 to Robert L. Woods proposes a solution to this problem by providing a technique for obtaining a direct indication of the partial pressure of a gas constituent in a mixture relative to a reference gas. Woods utilizes fluidic concentration sensors of the type disclosed in U.S. Pat. No. 3,771,348 to Villarroel and in U.S. Pat. No. 3,756,068 to Villarroel et al. and operates the device on the premise that the bridge pressure across the device can be scheduled to follow the ambient pressure by using an aspirator with the proper functional characteristics.

The equation which is the basis for operation in the Woods' technique is $$\Delta P_o = G K_1 C_1 (P_{o2}) \quad (B-1)$$

wherein:
$\Delta P_o$ = bridge pressure output
$G$ = the sensor gain constant
$K_1$ = gas sensitivity constant
$P_{o2}$ = partial pressure of oxygen and
$C_1$ = a constant.

This equation is reached by assuming that the aspirator performance will result in $$P_b = C_1 P_a \quad (B-2)$$

wherein:
$P_b$ = bridge pressure drop and
$P_a$ = the ambient pressure.

Woods' technique also assumes that G in equation (B−1) is constant. However, this is not necessarily so, and $\Delta P_o$ will not be proportional to $P_{o2}$ as originally postulated. Indeed, with $P_b$ varying as shown in equation (B−2) $\theta$ (of which G is a function) will vary as $$\theta C_2 P_a^2 \quad (B-3)$$

where $C_2$ = constant.

The effect of equation (B−3) on the value of G as $P_a$ varies from 0.3 to 1.0 atmospheres is significant. The present invention, however, makes use of the variation of G with $P_a$ to obtain the desired function of partial pressure sensors.

SUMMARY AND OBJECTS OF THE INVENTION

It is therefore one object of this invention to provide a fluidic bridge concentration sensor that can be designed to function as a partial pressure sensor.

Another object of this invention is to provide a fluidic partial pressure sensor which can directly indicate the partial pressure of a gas in a mixture relative to a reference gas.

A further object of this invention is to provide a partial pressure sensor which can function in an environment where the ambient pressure can undergo wide variations.

A still another object of this invention is to provide a simple, lowcost, rugged, and yet highly reliable technique of measuring partial pressures.

A still further object of this invention is to provide a direct-indicating partial pressure sensor that can be designed so as to have no moving parts.

The foregoing and other objects of this invention are attained through the provision of a fluidic device which comprises a typical fluidic bridge sensor having a first and second input channel, one for receiving a reference gas, the other receiving a mixture gas, and a means for providing a negative pressure drop across the bridge. The fluidic bridge's geometry is so designed and structured so that if the pressure across the bridge is maintained constant, the pressure differential between the two channels thereby becomes directly proportional to the partial pressure of the gas constituent of interest.

BRIEF DESCRIPTION OF THE DRAWINGS

Various objects, features and attendant advantages of the present invention will be more fully appreciated as the same becomes better understood from the following detailed description of the present invention when considered in connection with the accompanying drawings, in which.

DETAILED DESCRIPTION OF A PREFERRED EMBODIMENT

Figure 1:
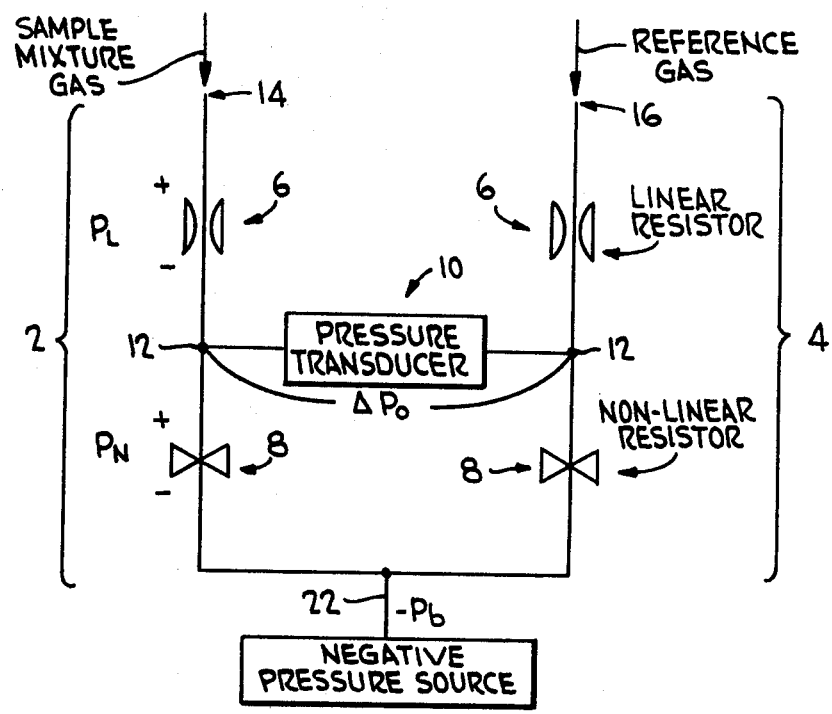
FIG. 1 illustrates schematically a fluidic bridge concentration sensor which may be utilized as part of this invention.

Referring now to the drawings, and more particularly to FIG. 1 thereof, there is depicted schematically a fluidic bridge concentration sensor which is utilizable in the present invention. The sensor consists of two identical flow channels 2 and 4 each of which comprises a linear resistor 6 and a nonlinear resistor 8. A negative pressure ($P_b$) is applied to the bridge at common outlet channel 22. The vacuum source here may be any conventional vacuum source. A pressure transducer 10 of any well known type such as an electronic pressure transducer of monometer is placed between the two channels at junction 12 between the linear and nonlinear resistors to measure the pressure differential between the two channels. The sensor includes a pair of inputs 14 and 16 exposed to ambient pressure to which are applied a reference gas and a sample mixture gas which contains the gas constituent whose partial pressure is to be measured within the reference gas. For further information concerning such sensors reference is made to Harry Diamond Laboratories' Report TM 73-9 entitled "Analog Flueric Gas Concentration Sensor" by F. Villarroel and R. L. Woods dated June, 1973 and Villaroel's U.S. Pat. No. 3,711,348 under the same title.

As detailed in U.S. Pat. No. 4,008,601 to Woods, the equations describing the performance of the bridge as a concentration sensor can be linearized to yield the following:

$$\frac{\Delta P_o}{P_b} = G K_1 X_s \tag{1}$$

where $\Delta P_o$ = output pressure signal of the bridge circuit $P_b$ = pressure drop across the bridge $K_1$ = gas sensitivity constant and $X_s$ = volume concentration of gas being measured in mixture channel.

The term G in equation (1) is defined as $$G = \frac{\sqrt{1+4\theta} - 2\theta - 1}{2\theta \sqrt{1+4\theta}} \tag{2}$$

where $$\theta = \frac{bpP_b}{(a\mu)^2} \tag{3}$$

and wherein $a$ and $b$ = the geometric constants for the linear and non linear resistors
$\rho$ = the density of the reference gas and
$\mu$ = the viscosity of the reference gas.

Assume that temperature is relatively constant, so that $\mu$ = constant. The density, $\eta$, will vary with $P_a$ as shown in equation (4)

$$\rho = \frac{P_a}{RT} = C_1 P_a \tag{4}$$

where $C_1$ is constant.
Substituting equation (4) into (3) yields $$\theta = \frac{bC_1 P_a P_b}{(a\mu)^2} \tag{5}$$

If we now assume that $P_b$, the bridge pressure, will be maintained constant, then equation (5) can be rewritten as $$\theta = C_2 P_a \tag{6}$$

where $$C_2 = \frac{bC_1 P_b}{(a\mu)^2} = \text{constant}.$$

Figure 2:
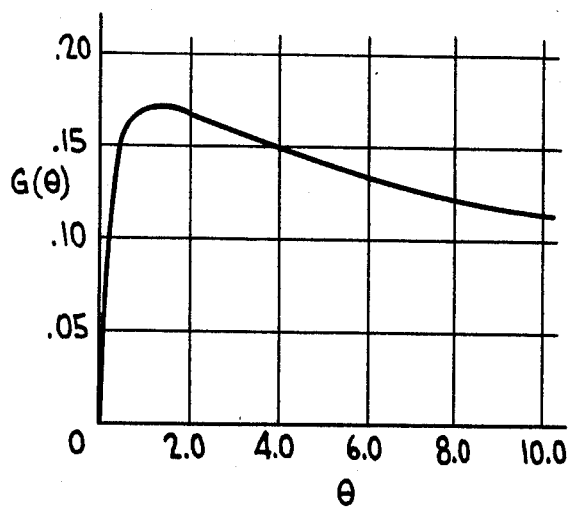
FIG. 2 illustrates graphically a complete plot of sensor gain (G) vs $\theta$.
Figure 3:
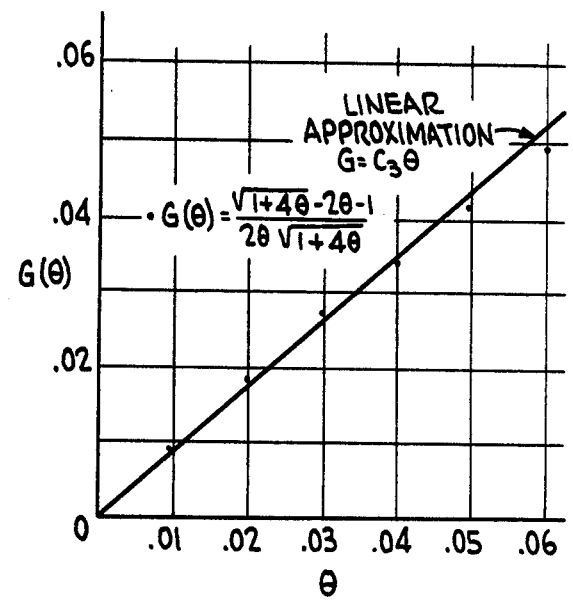
FIG. 3 illustrates graphically the initial portion of the plot of sensor gain (G) vs $\theta$ which is utilized in this invention.

Although the complete plot of G vs $\theta$ (eq. 2) is very non-linear as shown in FIG. 2, the initial portion of that curve is very close to linear for $\theta$ up to 0.05 as shown in FIG. 3. As $\theta$ increases beyond 0.05, the linearity approximation rapidly deteriorates. However, for $\theta$'s of 0.05, the less, the relationship between G and $\theta$ can be closely approximated by $$G = C_3 \theta \tag{7}$$

$C_3$ is the slope (constant) of the straight line approximation shown in FIG. 3.
Substituting equation (6) into (7) yields $$G = C_2 C_3 P_a \tag{8}$$

Now substituting equation (8) into (1) yields $$\frac{\Delta P_o}{P_b} = C_2 C_3 P_a K_1 X_s \tag{9}$$

But $P_b$, $C_2$, $C_3$, and $K_1$ are all constants, dependent on geometry selection, but independent of variations in $P_a$. In addition $P_s$, the partial pressure of the gas constituent of interest, is defined as $X_s P_a$. Therefore equation (9) simplifies to $$\Delta P_o = C_4 P_s \tag{10}$$

where $C_4 = C_2 C_3 P_b K_1$.

Figure 6:
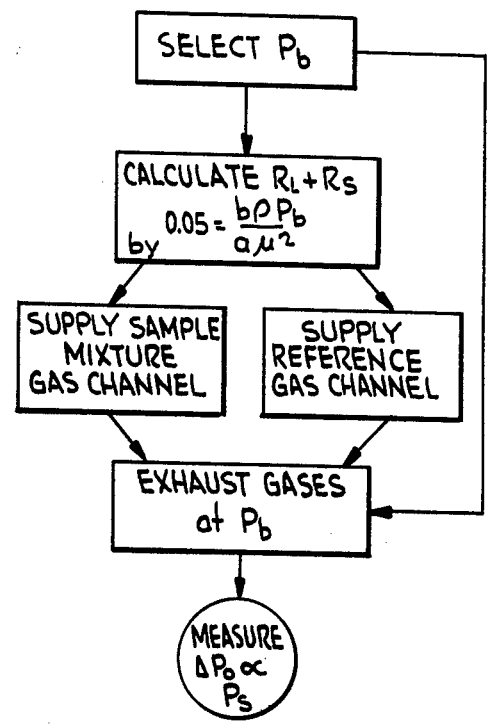
FIG. 6 illustrates by means of a flow chart the steps involved in the instant technique.

Equation (10) thus becomes the governing expression upon which this disclosure is based. Therefore if one knows the system requirements and the reference gas make-up the system can be designed by:

(1) Selecting a $P_b$ (bridge pressure) compatible with system criteria and
(2) Designing the geometry of the linear and nonlinear resistors by assigning $\theta = 0.05$ at the highest $P_a$ anticipated during operation. Therefore as $P_a$ decreases from that maximum value, $\theta$ will decrease and thereby always remain within that portion of the G - vs $-\theta$ curve that is most linear. FIG. 6 further summarizes this process in conjunction with the operation of fluidic bridge.

Equation (1) was reached using the linearized output equation for the bridge which is accurate for small values of $X_s$, but which can produce significant errors as $X_s$ increases beyond 0.20. With this in mind, the complete equation for the bridge $$\frac{\Delta P_o}{P_b} = \frac{\sqrt{1 + 4K\theta_r} - 1}{2K\theta_r} - \frac{\sqrt{1 + 4\theta_r} - 1}{2\theta_r}$$

where $K =$ $$K = \frac{(\frac{\rho}{\mu^2})\, mix}{(\frac{\rho}{\mu^2})\, ref}$$

is used in the calculations that follow to determine how effective the method presented in this disclosure would be in measuring partial pressure.

Let us consider the case of an $O_2$ partial pressure sensor. In an aircraft life support system it is desired to maintain a given partial pressure of $O_2$ ($P_{o2}$) within specific limits while the ambient varies between 0.3 and 1.0 atmospheres. Therefore that $P_{o2}$ is to be maintained at 160 mm Hg (the equivalent amount of $O_2$ in air at sea level). Assuming other gases are removed or can be ignored, the reference gas is nitrogen ($N_2$), and mixture gas is $N_2 + O_2$.

Figure 4:
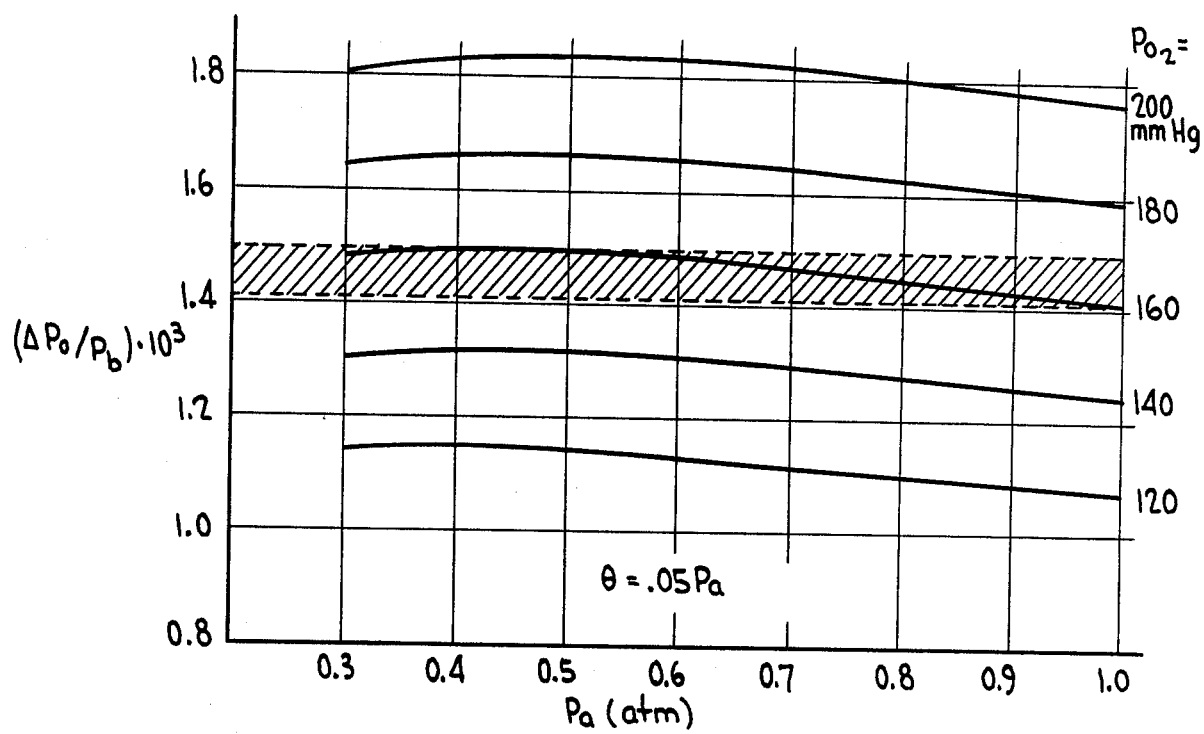
FIG. 4 illustrates graphically the sensor outputs when calculated for a $P_{o2}$ of 160 mm Hg at ambient pressures from 0.3 to 1.0 atmospheres when $\theta$ = 0.05 at 1.0 atmospheres.

The sensor outputs are then calculated for a $P_{o2}$ of 160 mm Hg at ambient pressures from 0.3 to 1.0 atm, selecting the value of $C_2$ in equation (6) as 0.05 (so that $\theta = 0.05$ at 1.0 atm). This procedure is repeated for other values of $P_{o2}$. The results are plotted in FIG. 4. Ideally, these curves would each of straight lines of zero slope. The sensor performance, while not ideal, shows that any given partial pressure could be measured within 10 mm Hg or better for ambient pressures of 0.3 to 1.0 atm. Furthermore, in actual use such a system would probably operate most of the time between 0.3 and 0.8 atm for which errors are even smaller.

Figure 5:
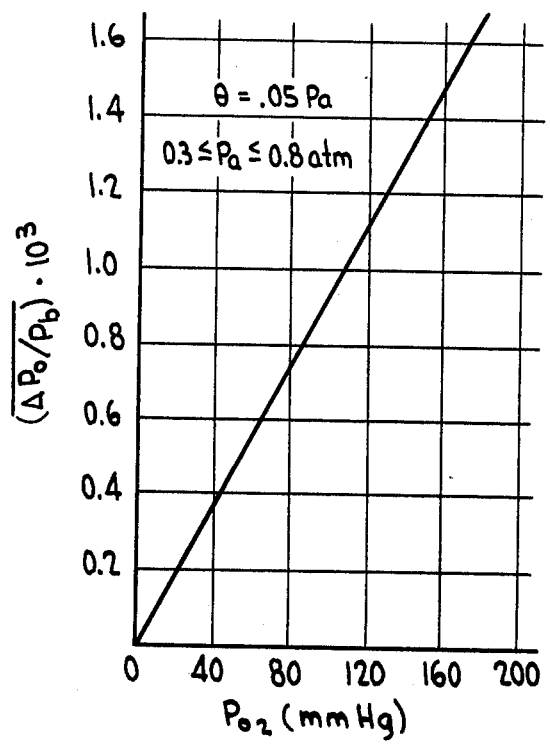
FIG. 5 illustrates graphically a plot of average sensor outputs $\Delta P_{o/Pb}$ vs partial pressure of oxygen ($P_{o2}$).

A closer examination of the predicted outputs for $P_a$ between 0.3 and 0.8 atm reveals that an average value of $\Delta P_o/P_b$ can be determined for each $P_{o2}$ such that the deviation from the average is only about 2 percent or less for $P_{o2}$ values between 100 and 180 mm Hg. A plot of these average outputs ($\Delta P_o/P_b$) vs $P_{o2}$, shown in FIG. 5, indicates a very linear relationship.

At a value of $\theta = 0.05$, the value of G is only about 25 percent of the maximum obtainable value which occurs at $\theta = 1.207$. Although this means the overall signal level produced is considerably less than maximum, this point is overshadowed by the fact that the bridge output will produce direct indication of partial pressure for $\theta$'s of approximately 0.05 and below and only in that region. Since the output signal levels are low it would perhaps be desirable to amplify for convenient measurement.

In summary, this disclosure describes a method by which the fluidic bridge gas-concentration sensor can be used to measure partial pressure directly. The sensor offers a simple, low-cost, highly reliable method to measure partial pressures. There is tremendous potential for such sensors in areas such as controlling breathing gases in life-support systems aboard military aircraft. Obviously modification and variations of the present invention are possible in light of the above teachings. It is therefore to be understood that within the scope of the appended claims the invention may be practiced otherwise than as specifically described herein.

What I claim as my invention is:

1. A fluidic partial pressure sensor for obtaining direct indication of the partial pressure of gas constituent in a mixture which comprises:
   a first input channel for receiving a reference gas;
   a second input channel for receiving a sample mixture gas;
   a fluidic bridge which comprises a pair of linear resistors connected respectively to each of the input channels, a pair of non-linear resistors connected at a first junction in series to each of the linear resistors and at a second junction to a reference output channel, and means for sensing pressure across the bridge; and
   a means for creating a constant pressure drop across the fluidic bridge, wherein the characteristics of the linear and non-linear resistors' geometry is determined by the equation $$\theta = \frac{b\rho P_b}{(a\mu)^2}$$

where
   $P_b$ = the pressure drop across the bridge
   $a$ and $b$ = geometric constants for the linear and non-linear resistors in the bridge circuit
   $\rho$ = the density of the reference gas
   $\mu$ = the viscosity of the reference gas and
   $\theta$ has a value of approximately 0.05 or less at the anticipated ambient pressures at which the sensor will operate.

2. The apparatus as set forth in claim 1 wherein $\theta$ is given a value of 0.05 at the highest anticipated ambient pressure at which the sensor will operate.

3. The apparatus as set forth in claim 2 wherein the means for creating a constant pressure drop across the bridge is a negative pressure device.

4. The apparatus as set forth in claim 3 wherein the means for sensing the pressure differential between the channels of the bridge is a pressure transducer operating between measurement ports at the first junction between the linear and nonlinear resistors.

5. A method for obtaining a direct indication of the partial pressure of a first gas in a reference gas by means of a fluidic bridge sensor containing a first and second channel, each having a linear and nonlinear resistor, and an outlet common to each of the channels, comprising the steps of:
   selecting the bridge pressure drop compatible with system criteria;
   selecting the geometries of the bridge resistors according to the equation $$\theta = \frac{b\rho P_b}{(a\mu)^2}$$

where
   $P_b$ = the pressure drop across the bridge
   $a$ and $b$ = geometric constants for the linear and non-linear resistors in the bridge circuit
   $\rho$ = the density of the reference gas
   $\mu$ = the viscosity of the reference gas and
   $\theta$ has a value of approximately 0.05 or less at the anticipated ambient pressures at which the sensor will operate;
   supplying the fluidic bridge concentration sensor with the reference gas in the first channel and with a sample mixture gas comprising the first gas whose partial pressure is desired to be measured in the reference gas in the second channel of the sensor;
   exhausting the sample mixture gas and the reference gas through the common outlet which is maintained at a constant pressure; and
   measuring the pressure difference across the bridge channels, thereby obtaining a signal output which provides a pressure directly proportional to the partial pressure of the first gas in the reference gas.

6. The method as set forth in claim 5 also comprising the step of determining the highest anticipated ambient pressure at which the sensor will operate.

7. The method as set forth in claim 6 wherein $\theta = 0.05$ at the highest anticipated ambient pressure at which the sensor will operate.

8. A fluidic partial pressure sensor for obtaining direct indication of the partial pressure of gas constituent in a mixture which comprises:
- a first input channel for receiving a reference gas;
- a second input channel for receiving a sample mixture gas;
- a fluidic bridge which comprises a linear resistor and a nonlinear resistor connected to each of the input channels and at a common junction to a reference output channel, and means for sensing pressure across the bridge; and
- a means for creating a constant pressure drop across the fluidic bridge, wherein the characteristics of the linear and non-linear resistor's geometry is determined by the equation $$\theta = \frac{b\rho P_b}{(a\mu)^2}$$

where
- $P_b$ = the pressure drop across the bridge
- $a$ and $b$ = geometric constants for the linear and non-linear resistors in the bridge circuit
- $\rho$ = the density of the reference gas
- $\mu$ = the viscosity of the reference gas and
- $\theta$ has a value of approximately 0.05 or less at the anticipated ambient pressures at which the sensor will operate.

* * * * *